United States Patent
Bowers et al.

(10) Patent No.: US 6,284,854 B1
(45) Date of Patent: *Sep. 4, 2001

(54) POLYMERIC SURFACE COATINGS

(75) Inventors: Roderick W. J. Bowers; Stephen A. Jones; Peter W. Stratford, all of Surrey (GB)

(73) Assignee: Biccompatibles Limited, Surrey (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/074,407

(22) Filed: May 8, 1998

Related U.S. Application Data

(63) Continuation-in-part of application No. 09/058,780, filed on Apr. 13, 1998, now abandoned, which is a continuation-in-part of application No. 08/474,472, filed on Jun. 7, 1995, now Pat. No. 5,739,236, which is a continuation of application No. 08/175,348, filed on Mar. 7, 1994, now Pat. No. 5,648,442.

(30) Foreign Application Priority Data

| Jul. 5, 1991 | (GB) | 9114619 |
|---|---|---|
| Aug. 8, 1991 | (GB) | 9117170 |
| Apr. 24, 1992 | (GB) | 9208970 |
| Jul. 6, 1992 | (WO) | PCT/GB92/01215 |

(51) Int. Cl.⁷ ........................ C08F 220/34; C08F 220/36; C08F 220/38

(52) U.S. Cl. .......................... 526/288; 526/287; 526/242; 526/243; 526/248; 526/253; 526/279; 526/304; 526/310; 526/312; 526/327; 526/328.5

(58) Field of Search .................................... 526/288, 287, 526/310, 312, 327, 328.5, 279, 242, 243, 248, 253, 304

(56) References Cited

U.S. PATENT DOCUMENTS

| 3,497,482 | * | 2/1970 | Hwa | 526/287 |
|---|---|---|---|---|
| 3,549,605 | * | 12/1970 | Dykstra . | |
| 5,311,223 | * | 5/1994 | Vanderlaan | 351/160 H |
| 5,389,383 | * | 2/1995 | Huth | 424/912 |
| 5,516,887 | * | 5/1996 | Deghenghi | 530/313 |
| 5,686,066 | * | 11/1997 | Harada | 424/70.17 |
| 5,747,014 | * | 5/1998 | Cauwet | 424/70.11 |
| 5,747,016 | * | 5/1998 | Yui | 424/401 |
| 5,789,399 | * | 8/1998 | Strube | 514/167 |

* cited by examiner

Primary Examiner—Fred Zitomer
(74) Attorney, Agent, or Firm—Sughrue, Mion, Zinn, Macpeak & Seas, PLLC

(57) ABSTRACT

A non-crosslinked biocompatible polymer is formed from a radical polymerisable ethylenically unsaturated zwitterionic monomer containing a sulpho-betaine zwitterionic group and a radical polymerisable ethylenically unsaturated comonomer containing a hydrophobic group selected from $C_{6-24}$-alkyl, $C_{1-24}$-fluoroalkyl and siloxane groups. Suitable copolymers are of N,N-dimethyl ammonium-N-propylsulphonate-N-ethyl methacrylate and dodecyl-methacrylate. The polymer may be used to coat substrates to render them biocompatible, especially hemocompatible. The hydrophobic groups render the polymer particularly suitable for coating hydrophobic substrates.

12 Claims, No Drawings

POLYMERIC SURFACE COATINGS

This is a Continuation-in-Part of application Ser. No. 09/058,780 filed Apr. 13, 1998 now abandoned which is a continuation-in-part of application Ser. No. 08/474,472 filed Jun. 7, 1995 U.S. Pat. No. 5,739,236 which is a continuation of application Ser. No. 08/175,348 filed Mar. 7, 1994 U.S. Pat. No. 5,648,442, which was derived from UK Patent Application No. 9114619.1 filed Jul. 5, 1991; UK Patent Application No. 9117170.2 filed Aug. 8, 1991 and UK Patent Application No. 9208970.5 filed Apr. 24, 1992, and International Application No. PCT/GB92/01215 filed Jul. 16, 1992.

The present invention relates to new polymers, processes for producing them and processes for coating surfaces with them. The invention also provides improved processes for producing certain monomers and to certain new monomers used to obtain the polymers. The polymers are useful for coating surfaces of devices and materials which come into contact with protein-containing solutions and biological fluids, and rendering the surfaces bio- and haemocomaptible. Surfaces may thus be rendered suitable for prolonged contact with living tissues and body fluids and with protein-containing solutions.

Materials used in the manufacture of separation substrates and devices, blood contacting devices contact and intraocular lenses, and other devices which are used in contact with protein-containing or biological fluids must be selected on the basis of acceptable physical and mechanical properties and compatibility with the protein-containing or biological fluid. For any given application of these materials it is usually difficult to optimise all of these considerations simultaneously and a compromise must be reached often resulting in less than optimal performance. For example, major biological problems are often encountered with materials which have otherwise optimal mechanical and physical properties. These problems often manifest themselves as undesirable deposition of biological components and in particular proteinaceous material. This protein adsorption results in blood clot formation in blood-contacting materials, the adsorption of tear components onto contact lenses resulting in deposit formation, formation of deposits on intraocular lenses and in separation media it results in blockage and failure of separation devices. Such effects lead to significant loss in operational performance and often complete rejection and failure of devices.

In the case of medical devices, for example prostheses and components of blood dialysis equipment, it is common practice to employ biocompatible polymers to form at least the surface of the devices to discourage protein adsorption. However, these materials are not perfect and reaction with the living tissues still remains a problem; for example surface-induced thrombosis is still a major difficulty, particularly where large quantities of blood are contacted with a foreign surface such as in artificial lungs and kidneys. Formation of a clot in an artificial organ has a number of adverse or even catastrophic effects including occlusion of the blood pathway in the extracorporeal system, or embolism if the clot breaks off the artificial surface and lodges in a host blood vessel. Dialysis membranes, heart valves, circulator-assist devices, blood substitutes and artificial lungs all share this problem.

It is known that materials for use as biocompatible coatings should ideally:
(a) be capable of reproducible manufacture as pure materials;
(b) be capable of being coated onto surfaces without being degraded or adversely changed;
(c) have the requisite mechanical and permeability properties required for the specific function of the device for which they are intended;
(d) be sterilisable without adverse changes in, for example, permeability and mechanical or surface properties;
(e) not be damaged or degraded by the biological environment;
(f) not be carcinogenic.

In applications involving direct contact with blood further restrictions exist. Materials should not:
(g) induce significant platelet adhesion;
(h) interfere with the normal clotting mechanism; or
(i) cause any significant damage to the cellular elements or soluble components of the blood.

There have been many attempts to prepare biocompatible, and specifically blood compatible (i.e. haemocompatible), surfaces, which do not activate the blood coagulation process and do not promote thrombus formation. Examples of such attempts include the preparation of negatively charged surfaces, such as by use of anionic polymers or suitable oriented electret polymers, preparation of surfaces coated with the natural anticoagulant heparin or synthetic heparin analogues, preparation of surfaces with inherently low surface free energy such as by use of silicone rubber, preparation of albumin-coated surfaces, and preparation of surfaces coated with compounds such as some polymethanes which are thought to adsorb albumin preferentially from blood. All of these however have had limitations.

We have now devised new film-forming polymers which can be used to coat surfaces. It has been found that these copolymers may be used to provide stable coatings on a wide variety of surfaces including, polyethylene, PVC, steel and poly(imide). The invention also provides physiadsorbable polymers which when used to coat surfaces, do not swell, to any significant extent, in aqueous environments; in some situations swelling in aqueous environments can reduce the stability of coatings of physiadsorbable polymers on surfaces.

The polymers which contain zwitterionic groups, mimic the zwitterionic structure of phospholipids such as phosphatidylcholine and sphingomyelin which are the major components of the outer membrane of all living cells. In this way the present invention seeks to provide a biocompatible surface on a coated substrate at which the deposition of proteins and cells at the substrate is minimised when the coated substrate comes into contact with a protein-containing solution or biological fluid.

In addition a variety of ligands may be attached to the polymers of the present invention when coated onto a substrate. Alternatively ligands may be attached to the polymers prior to coating on a substrate, e.g. when the polymer is in solution. The polymers of the present invention may therefore provide a means of attachment of such ligands. The term ligand includes, but is not limited to, specific binding agents such as immunoglobulins and associated fragments thereof such as those useful for affinity separation and diagnostic applications, photosensitive and chemisensitive moieties such as those useful for detector and sensor applications and therapeutic agents useful for clinical applications. Other ligands include peptide fragments which may be chemically linked to a polymer of the invention, such as fragments which induce cell attachment and may therefore be used to allow the polymers of the present invention to provide cell seeding.

The present invention provides a polymer of one or more radical polymerisable, preferably ethylenically unsaturated, monomers, which polymer has pendant zwitterionic groups and other pendant groups capable of stably binding the polymer to a surface. Such coatings bind to surfaces with good adhesion and are not removable in the environment in which the coated surfaces are used, e.g. in use as a coating on a blood-contacting surface.

Without wishing to be limited by this theory, it is thought that the presence of zwitterionic groups at a surface renders the surface more biocompatible. The extent to which a polymer renders a surface biocompatible may be assessed as a combination of factors such as reduction in the extent to which the surface causes blood platelet activation, protein adsorption, (for instance as judged by absorption of fibrinogen from human plasma) and reaction with C-reactive protein which is caused by the presence on the surface of isolated zwitterionic, e.g.) phosphate ammonium ester groups. Preferably the polymers of the invention when coated onto a substrate, provide a reduction in platelet activation of at least 70%, more preferably at least 90%, as assessed by the assay described hereinafter compared to an untreated substrate. It is also preferred that the polymers of the invention, when coated onto a substrate, provide a reduction in fibrinogen absorption of at least 60% as assessed by the assay described hereinafter and a protein index of less than $1.5 \times 10^3$ compared to an untreated substrate. The protein index is defined as the ratio of the absorbance due to C-reactive protein measured in the assay described hereinafter to the reduction in fibrinogen adsorption.

The groups capable of binding the polymer to a surface will be selected depending upon the nature of the surface which it is intended to coat with the polymer. Where the surface is hydrophobic, hydrophobic groups capable of being physisorbed at the surface may be used to bind the polymer to the surface.

Polymers of the invention therefore bind to a surface by physisorption.

The hydrophobic groups capable of stably binding the polymer to a surface may be present in the same monomer and the zwitterionic group are in separate monomer species which are copolymerised to provide the polymer of the invention.

It will be understood that throughout, where a group is referred to as capable of binding a polymer to a surface this is intended to mean stably binding.

The hydrophobic groups are alkyl groups of 6 or more carbon atoms, or fluoroalkyl groups, optionally having one or more etheric oxygen atoms interrupting the carbon chain, and optionally containing one or more carbon—carbon double or triple bonds, or siloxane groups, preferably containing from 1 to 50, more preferably 5 to 30, silicon atoms, may be used as the pendant groups capable of binding the polymer to a surface. Such groups are capable of forming strong secondary valence interactions with a surface, and being physisorbed at a hydrophobic surface, i.e. adsorbed without formation of a covalent interaction.

The present invention therefore provides a polymer obtained by copolymerising a radical polymerisable, ethylenically unsaturated, comonomer containing a zwitterionic group and a radical polymerisable ethylenically unsaturated, comonomer containing a radical polymerisable moiety and an alkyl group of 6 or more carbon atoms, which alkyl group optionally contains one or more etheric oxygen atoms and optionally one or more carbon—carbon double or triple bonds, or a fluoroalkyl group which optionally contains one or more etheric oxygen atoms and optionally one or more carbon—carbon double or triple bonds, or a siloxane group.

It is also preferred that the physisorbable group is an alkyl or fluoroalkyl group optionally containing one or more carbon—carbon double or triple bonds. Such a group may contain one or more etheric oxygen atoms, but in an especially preferred embodiment does not contain any etheric oxygen atoms.

In one embodiment, where the physisorbable group is an alkyl or fluoroalkyl group, optionally containing one or more etheric oxygen atoms, this group does not contain any carbon—carbon double or triple bonds.

Optionally the polymers also comprise residues of one or more diluent and/or crosslinkable monomers.

The invention also provides a process for producing such a polymer which comprises polymerising such monomers and a process for coating a surface with such a polymer, for instance a process comprising the steps of (a) polymerising such monomers to form the polymer and (b) coating the surface with the polymer so formed. Optionally, the process further comprises attaching a ligand to the polymer either in solution before coating the surface, or, more preferably when coated on the surface.

In a specific embodiment the invention further provides such polymers containing residues of a crosslinkable monomer, which are uncrosslinked, when either coated on a surface or not coated on a surface and such polymers which are crosslinked when coated on a surface. The invention further provides a process of crosslinking such polymers when coated on a surface.

As yet a further feature, the present invention provides certain new monomers useful in producing the polymers of the invention.

Monomers and comonomers which may be used in the polymers of the invention will now be described in more detail.

It is to be understood that throughout the specification (alk)acrylate, (alk)acrylic and (alk)acrylamide mean acrylate or alkacrylate, acrylic or alkacrylic and acrylamide or alkacrylamide respectively. Preferably unless otherwise stated alkacrylate, alkacrylic and alkacrylamide groups contain from 1 to 4 carbon atoms in the alkyl group thereof and are most preferably methacrylate, methacrylic or methacrylamide groups. Similarly (meth)acrylate, (meth)acrylic and (meth)acrylamide shall be understood to mean acrylate or methacrylate, acrylic or methacrylic and acrylamide or methacrylamide respectively.

Zwitterionic Monomers

The zwitterionic monomer (or comonomer) typically the centre of permanent positive charge is provided by a quaternary nitrogen atom.

Preferred zwitterionic monomers are of general formula (I)

$$Y\text{---}B\text{---}X \tag{I}$$

wherein B is a straight or branched alkylene, oxaalkylene or oligo-oxaalkylene chain optionally containing one or more fluorine atoms up to and including perfluorinated chains or, if x contains a carbon—carbon chain between B and the centre of permanent positive charge or if Y contains a terminal carbon atom bonded to B, a valence bond;

X is a zwitterionic group and

Y is an ethylenically unsaturated polymerisable group selected from

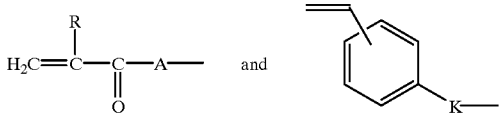 and wherein:
R is hydrogen or a $C_1$–$C_4$ alkyl group;
A is —O— or —$NR^1$— where $R^1$ is hydrogen or a $C_1$–$C_4$ alkyl group or $R^1$ is —B—X where B and X are as defined above; and
K is a group —$(CH_2)_pOC(O)$—, —$(CH_2)_pC(O)O$—, —$(CH_2)_pOC(O)O$—, —$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pOC(O)NR^2$—, —$(CH_2)_pNR^2C(O)NR^2$—, (in which the groups $R^2$ are the same or different) —$(CH_2)_pO$—, —$(CH_2)_pSO_3$—, or, optionally in combination with B, a valence bond and p is from 1 to 12 and $R^2$ is hydrogen or a $C_1$–$C_4$ alkyl group.

The proviso on whether B may be a valence bond ensures that the centre of permanent positive charge in X is not directly bonded to a heteroatom, such as an oxygen or nitrogen atom in Y.

Preferred monomers containing a group bearing a centre of permanent positive charge are therefore of general formula (II) or (III).

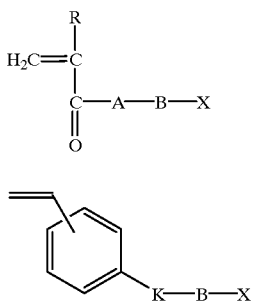

(II)

(III)

where R, A, B, K and X are as defined with reference to formula (I).

Preferably in the compounds of formula (II) R is hydrogen, methyl, or ethyl, more preferably methyl, so that (II) is an acrylic acid, methacrylic acid or ethacrylic acid derivative.

In the compounds of formula (III) K may be a valence bond and B a group, K may be a group and B a valence bond, both K and B may be groups, or K and B may together be a valence bond.
Preferably B is a group where K is a valence bond.

Where K is a group then preferably p is from 1 to 6, more preferably 1,2 or 3 and most preferably p is 1. When K is a group —$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pOC(O)NR^2$— or —$(CH_2)_pNR^2C(O)NR^2$— then $R^2$ is preferably hydrogen, methyl or ethyl, more preferably hydrogen.

In the compounds of formula (III) preferably the vinyl group is para to the group —K—B—X.
Preferably B is:
an alkylene group of formula —$(CR^3_2)_a$—, wherein the groups —$(CR^3_2)_a$— are the same or different, and in each group —$(CR^3_2)_a$— the groups $R^3$ are the same or different and each group $R^3$ is hydrogen, fluorine or $C_{1-4}$ alkyl or fluroalkyl, preferably hydrogen, and a is from 1 to 12, preferably 1 to 6;
an oxaalkylene group such as alkoxyalkyl having 1 to 6 carbon atoms in each alkyl moiety, more preferably —$CH_2O(CH^2)_4$—; or
an oligo-oxaalkylene group of formula —$[(CR^4_2)_bO]_c(CR^4_2)_b$— where the groups —$(CR^4_2)$— are the same or different and in each group —$(CR^4_2)$— the groups $R^4$ are the same or different and each group $R^4$ is hydrogen, fluorine or $C_{1-4}$ alkyl or fluoroalkyl, preferably hydrogen, and b is from 1 to 6, preferably 2 or 3 and c is from 2 to 11, preferably 2 to 5; or
if X contains a carbon—carbon chain between B and the centre of permanent positive charge or if Y contains a terminal carbon atom, a valence bond.

Preferred groups B include alkylene, oxaalkylene and oligo-oxaalkylene groups of up to 12 carbon atoms optionally containing one or more fluorine atoms. Where the polymer is not intended for coating a hydrophobic surface, and therefore is not intended to be bound by physiosorption to a surface, then preferably B is an alkylene, oxaalkylene or oligo-oxaalkylene group which does not contain any fluorine atoms.

In compounds of formula (III) it is preferred that K and B contain up to 12 carbon atoms in total.

Groups X are the groups of formula (IVB). The groups of formula (IVB) are:

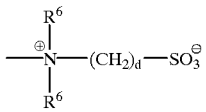

(IVB)

where the groups $R^6$ are the same or different and each is hydrogen or $C_{1-4}$ alkyl and d is from 2 to 4.

Preferably the groups $R^6$ are the same. It is also preferable that at least one of the groups $R^6$ is methyl, and more preferable that the groups $R^6$ are both methyl.

Preferably d is 2 or 3, more preferably 3.

Preferably B is a group of formula —$(CR^3_2)$— or —$(CR^3_2)2$ eg. —$(CH_2)$— or —$(CH_2CH_2)$—.

Zwitterionic monomers of formula (II) and (III) may be prepared by conventional techniques using known reactions, for example using a suitable substituted alkyl (alk)acrylate or suitable substituted styrene as precursor. Examples of suitable substituted alkyl (alk)acrylates include dimethylaminoethyl(meth)acrylate and 2-hydroxyethyl (meth)acrylate.

Monomers containing a group of formula (IVB) may be prepared as described in Reference Example 1 or by analogous known methods.

a) Comonomers Containing an Alkyl, Fluoroalkyl or Siloxane Group

The comonomers containing an alkyl, fluoroalkyl or siloxane group, which are suitable for providing binding to a hydrophobic surface, are comonomers containing an alkyl group of 6 or more carbon atoms which group optionally contains one or more etheric oxygen atoms and optionally one or more carbon—carbon double or triple bonds or a fluoroalkyl group, preferably of 6 or more carbon atoms, which group optionally contains one or more etheric oxygen atoms and optionally one or more carbon—carbon double or triple bonds, or containing a siloxane group, containing up to 50 silicon atoms, preferably in a linear chain.

Preferably the alkyl or fluoroalkyl groups contains up to 24 carbon atoms, for instance up to 18 carbon atoms, or containing a siloxane group, containing up to 50 silicon, preferably in a linear chain. Preferred comonomers containing an alkyl, fluoroalkyl or siloxane group are those of general formula (VI)

where $Y^1$ is an ethylenically unsaturated polymerisable group selected from

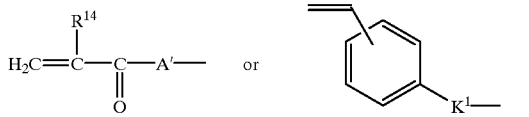

where $R^{14}$ is hydrogen or $C_1$–$C_4$ alkyl,

A' is —O— or —NR$^{15}$— where $R^{15}$ is hydrogen or a $C_1$–$C_4$ alkyl group or $R^{15}$ is a group Q;

$K^1$ is a group —(CH$_2$)$_1$OC(O)—, —(CH)$_1$C(O)O—, —(CH$_2$)$_1$OC(O)O—, —(CH$_2$)$_1$NR$^{16}$—, —(CH$_2$)$_1$NR$^{16}$C(O)—, —(CH$_2$)$_1$C(O)NR$^{16}$—, —(CH$_2$)$_1$NR$^{16}$C(O)O—, —(CH$_2$)$_1$OC(O)NR$^{16}$—, —(CH$_2$)$_1$NR$^{16}$C(O)NR$^{16}$— (in which the groups $R^{16}$ are the same or different), —(CH$_2$)$_1$O—, —(CH$_2$)$_1$SO$_3$—, a valence bond and 1 is from 1 to 12 and $R^{16}$ is hydrogen or a $C_1$–$C_4$ alkyl group; and Q is (a) a straight or branched alkyl, alkoxyalkyl or (oligo-alkoxy)alkyl chain containing 6 or more, preferably 6 to 24, carbon atoms unsubstituted or substituted by one or more fluorine atoms and optionally containing one or more carbon—carbon double or triple bonds; or (b) a siloxane group —(CR$^{16a}$$_2$)$_{qq}$(SiR$^{16b}$$_2$)(OSiR$^{16b}$$_2$)$_{pp}$R$^{16b}$ in which each group R$^{16a}$ is the same or different and is hydrogen or alkyl of 1 to 4 carbon atoms or aralkyl, for example benzyl or phenethyl, each group R$^{16b}$ is alkyl of 1 to 4 carbon atoms, qq is from 1 to 6 and pp is from 0 to 49.

Preferred comonomers of formula (VI) bearing a group Q include those of formula (VII) and (VIII):

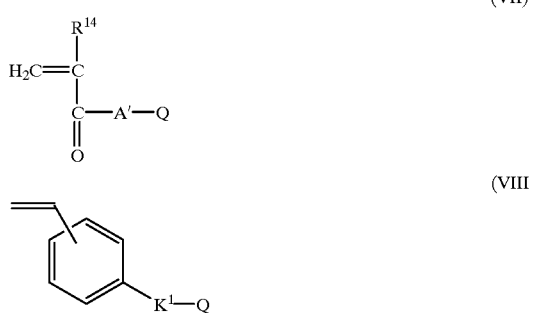

wherein:

$R^{14}$, A', $K^1$ and Q are as defined in relation to formula (VI).

Preferably in the compounds of formula (VII) $R^{14}$ is hydrogen methyl or ethyl, more preferably methyl so that the compound of formula (VII) is preferably an acrylic acid, methacrylic acid or methacrylic acid derivative.

In the compounds of formula (VIII) $K^1$ may for instance be a valence bond. Where $K^1$ is a group then preferably 1 is from 1 to 6, more preferably 1, 2 or 3 and most preferably 1 is 1. When $K^1$ is a group —(CH$_2$)$_1$NR$^{16}$—, —(CH$_2$)$_1$OC(O)NR$^{16}$—, —(CH$_2$)$_1$NR$^{16}$C(O)O—, —(CH$_2$)$_1$NR$^{16}$C(O)—, —(CH$_2$)$_1$C(O)NR$^{16}$— or —(CH$_2$)$_1$NR$^{16}$C(O)NR$^{16}$— then $R^{16}$ is preferably hydrogen, methyl or ethyl, more preferably hydrogen.

In the compounds of formula (VIII), preferably the vinyl group is para to the group —K$^1$—Q.

Preferably Q is an alkyl or fluoroalkyl group optionally containing one or more etheric oxygen atoms and optionally or more carbon—carbon double or triple bonds.

More preferably Q is:

an alkyl group of formula —(CR$^{17}$$_2$)$_m$CR$^{17}$$_3$ wherein the groups —(CR$^{17}$$_2$)— are the same or different, and in each group —(CR$^{17}$$_2$) the groups $R^{17}$ are the same or different and each group $R^{17}$ is hydrogen, fluorine or $C_{1-4}$ alkyl or fluoroalkyl and m is from 5 to 23 if Q contains no fluorine atoms or from 1 to 23, preferably 5 to 23, if Q contains one or more fluorine atoms;

an alkoxyalkyl having 1 to 12 carbon atoms in each alkyl moiety; unsubstituted or substituted by one or more fluorine atoms; or an (oligo-alkoxyl) alkyl group of formula —[(CR$^{18}$$_2$)$_n$O]$_o$(CR$^{18}$$_2$)$_n$R$^{18}$ where the groups —(CR$^{18}$$_2$)— are the same or different and in each group —(CR$^{18}$$_2$)— the groups $R^{18}$ are the same or different and each group $R^{18}$ is hydrogen, fluorine or $C_{1-4}$ alkyl or fluoroalkyl and n is from 2 to 6, preferably 3 to 4, and 0 is from 1 to 12.

When Q is a group —[(CR$^{18}$$_2$)$_n$O]$_o$(CR$^{18}$$_2$)$_n$R$^{18}$ wherein all the groups $R^{18}$ are hydrogen and in all the groups —[(CR$^{18}$$_2$)$_n$O]— n is 2 the group of formula Q is not able to form strong secondary valence interactions with hydrophobic surfaces. Whilst residues of monomers containing such a group may be included in the polymers of the invention, it is also necessary to include residues of monomers which are capable of forming such strong secondary valence interactions if such interactions are to bind a polymer to a surface. Monomers which have groups containing oligo(higher alkylene) oxide moieties can be used to provide monomers which contain oligo-alkylene oxide moieties in which at least 50 mol % of individual alkylene oxide units contain 3 or more carbons atoms. Thus, for instance a mixed oligo(ethylene oxide/propylene oxide) side chain could be used provided that there are more propylene oxide units than ethylene oxide units.

Where Q is an (oligo-alkoxy)-alkyl group containing residues —[(CR$^{18}$$_2$)$_n$O]— wherein n is 2, then preferably n is 2 in no more than 50 mol % of the residues —[(CR$^{18}$$_2$)$_n$O]—.

Alternatively, Q may be a group in which one or more of the alkyl or alkylene moieties in such an alkyl, alkoxyalkyl or (oligoalkoxy) alkyl group is replaced by a corresponding alkenyl, alkynyl, alkenylene or alkynylene moiety.

Preferred groups Q include alkyl, alkoxyalkyl and (oligo-alkoxy)alkyl groups optionally containing one or more carbon—carbon double or triple bonds of 8 or more, more preferably 10 or more, even more preferably 12 or more, for instance 14 or more, such as 16 or more carbon atoms. Such groups may contain one or more fluorine atoms and be therefore fluoroalkyl derivatives. Preferably however, such groups do not contain any fluorine atoms.

Particularly preferred groups are straight chain alkyl or fluoroalkyl groups optionally containing one or more carbon—carbon double or triple bonds.

Where Q is a siloxane group, each group —(CR$^{16a}$$_2$)— may be the same or different, preferably the same, and preferably each group $R^{16a}$ is hydrogen. Preferably qq is from 2 to 4, and is most preferably 3. Each group —(SiR$^{16b}_2$)— may be the same or different, preferably the same, and preferably each group R$^{16b}$ is methyl. Preferably pp is from 4 to 29. Preferred comonomers where Q is a siloxane group are those of formula (VII).

In one specific embodiment the group Q does not contain any ethylenic unsaturation, i.e. any carbon-carbon double or triple bonds.

Particular examples of comonomers containing an alkyl, fluoroalkyl or siloxane group include: n-dodecyl methacrylate, octadecyl methacrylate, hexadecyl methacrylate, 1H,1H,2H,2H-heptadecafluorodecyl methacrylate, p-octyl styrene, p-dodecyl styrene and monomethacryloxypropyl terminated siloxanes. n-Dodecyl methacrylate is particularly preferred.

Comonomers containing a physisorbable alkyl or fluoroalkyl, which does not contain a carbon—carbon double or triple bond, or a siloxane group such as those of formulae (VII) and (VIII) are commercially available or may be, prepared by conventional techniques using known reactions.

In a second specific embodiment of such comonomers, the group Q does contain ethylene unsaturation, i.e. one or more carbon—carbon double or triple bonds. Such comonomers may for example contain a vinylic, divinylic, acetylenic or diacetylenic moiety. Comonomers containing acetylenic rather than vinylic unsaturation are in general preferred, especially those containing a single acetylenic group.

Comonomers which contain such an ethylenic unsaturated group are capable of providing crosslinking between linear polymer claims once the polymer is coated onto a substrate, as well as binding to the substrate by physisorption. Such crosslinking may improve the stability of the coating and is typically formed by irradiation, for example with uv -or gamma-radiation. The crosslinking of such groups may be employed either alone or in addition to the use of a comonomer containing a reactive group as a crosslinkable comonomer as described below.

Particularly preferred crosslinkable comonomers capable of binding to a substrate by physisorption are those of formula (VIIA) and (VIIIA).

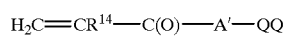
(VIIA)

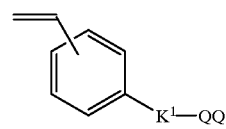
(VIIIA)

in which R$^{14}$, A' and K$^1$ are as hereinbefore defined and QQ is an alkynyl group containing 6 or more carbon atoms and one or two, preferably one, carbon—carbon triple bonds provided that the acetylenic moieties are not directly bonded to A' or K$^1$.

The present invention provides, as a further feature, comonomers of formula (VIIA) and (VIIIA).

Amongst such comonomers it is preferred that QQ is a group containing from 6 to 24 carbon atoms, preferably 8 or more, more preferably 10 or more, even more preferably 12 or more, for instance 14 or more, such as 16 or more carbon atoms.

It is also preferred that the group QQ does not contain a terminal acetylenic moiety, i.e. a group —C≡CH.

A particularly preferred group QQ is 7-dodecynyl and a specific example of a compound of formula (VIIA) containing such a group is dodec-7-yn-1-ol methacrylate.

The compound of formula (VIIA) and (VIIIA) and other comonomers of formula (VII) and (VIII) containing an ethylenically unsaturated physisorable group Q, may be prepared by analogy with known methods. Their preparation is illustrated by Reference Example 5.

b) Comonomers Bearing a Reactive Group

Preferred comonomers, which are suitable for providing crosslinking, contain a reactive group capable of crosslinking by reaction with coreactive groups on the polymer and are of general formula (IX)

(IX)

where Y$^2$ is an ethylenically unsaturated polymerisable group selected from

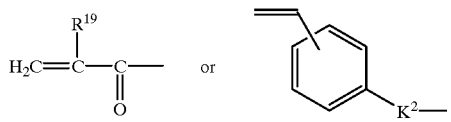

where R$^{19}$ is hydrogen or C$_1$–C$_4$ alkyl,

K$^2$ is a group —(CH$_2$)$_q$OC(O)—, —(CH)(C(O)O—, —(CH$_2$)$_q$OC(O)O—, —(CH$_2$)$_q$NR$^{20}$—, —(CH$_2$)$_q$NR$^{20}$OC(O)—, —(CH$_2$)$_q$C(O)NR$^{20}$—, —(CH$_2$)$_q$NR$^{20}$C(O)O—, —(CH$_2$)$_q$OC(O)NR$^{20}$—, —(CH$_2$)$_q$NR 20C(O)NR$^{20}$— (in which the groups R$^{20}$ are the same or different), —(CH$_2$)$_q$O—, or —(CH$_2$)$_q$SO$_3$—, or a valence bond and q is from 1 to 12 and R$^{20}$ is hydrogen or a C$_1$–C$_4$ alkyl group; and Q$^1$ is a reactive group capable of reacting to provide covalent binding to a surface.

Preferred comonomers of formula (IX) bearing a reactive group Q$^1$ include those of formula (X) and (XI) defined below.

The compounds of formula (X) are:

(X)

wherein:

R$^{19}$ is as defined with reference to formula (X), and Q$^2$ is a reactive group.

Preferably in the compounds of formula (X) R$^{19}$ is hydrogen, methyl or ethyl, more preferably methyl, so that the compound of formula (X) is preferably an acrylic acid, methacrylic acid or ethacrylic acid derivative.

Preferably Q$^2$ is hydrogen, or more preferably —OH or a group of the formula:

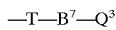

where

T is —O—, or —NR$^{21}$— where R$^{21}$ is hydrogen, C$_1$–C$_4$ alkyl or a group —B$^7$—Q$^3$;

B$^7$ is a valence bond or, more preferably, a straight or branched alkylene, oxaalkylene or oligo-oxaalkylene chain; and Q$^3$ is a reactive group capable of reacting to provide covalent binding to a surface such as an aldehyde group or a silane or siloxane group containing one or more reactive substituents such as halogen, for example chlorine, or alkoxy, generally containing from 1 to 4 carbon atoms, for example methoxy or ethoxy, or, more preferably $Q_3$ is a hydroxyl, amino, carboxyl, epoxy, —CHOHCH$_2$Hal, (in which Hal is a halogen atom such as chlorine, bromine or iodine) succinimido, tosylate such as 2(N-methylpyridinium) tosylate, triflate, imidazole carbonyl-amino, or an optionally substituted triazine group.

Preferably $B^7$ is:

an alkylene group of formula —(CR$^{22}_2$)$_r$— wherein the groups —(CR$^{222}$)— are the same or different, and in each group —(CR$^{22}_2$)— the groups R$^{22}$ are the same or different and each group R$^{22}$ is hydrogen or C$_{1-4}$ alkyl, preferably hydrogen, and r is from 1 to 12, preferably 1 to 6;

an oxaalkylene group such as alkoxyalkyl having 1 to 6 carbon atoms in each alkyl moiety; or an oligo-oxaalkylene group of formula —[(CR$^{23}_2$)$_s$O]$_t$(CR$^{23}_2$)$_s$— where the groups —(CR$^{23}_2$)— are the same or different and in each group —(CR$^{23}_2$)— the groups R$^{23}$ are the same or different and each group R$^{23}$ is hydrogen or C$_{1-4}$ alkyl, preferably hydrogen, and s is from 1 to 6, preferably 2 or 3, and t is from 1 to 11, preferably 1 to 5.

Preferred groups $B^7$ include alkylene, oxaalkylene and oligo-oxaalkylene groups of up to 12 carbon atoms.

Where $Q^3$ is a silane or siloxy group, preferably $B^7$ is an alkylene group of 1 to 6, preferably 2 to 4, more preferably 3 s carbon atoms.

Particular examples of the group $B^7$ are —CH$_2$—, —CH$_2$CH$_2$— and —(CH$_2$)$_6$—.

The compounds of formula (XI) are:

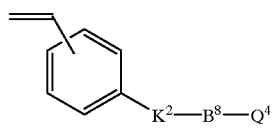

(XI)

wherein $K^2$ is as defined in relation to formula (IX) and;

$B^8$ is a straight of branched alkylene, oxaalkylene or oligo-oxaalkylene chain and $Q^4$ is a reactive group capable of reacting to provide covalent binding to a surface, for example an aldehyde group or a silane or siloxane group containing one or more reactive substituents such as halogen, for example chlorine, or alkoxy, generally containing from 1 to 4 carbon atoms, for example methoxy or ethoxy, or, more preferably, $Q^4$ is a hydroxyl, amino, carboxyl, epoxy, —CHOHCH$_2$Hal, (in which Hal is a halogen atom such as chlorine, bromine or iodine) succinimido, tosylate, triflate, imidazole carbonyl-amino or optionally substituted triazine group.

In the compounds of formula (XI) preferably the vinyl group is para to the group —K$^2$—B$^8$—Q$^4$.

$K^2$ may for instance be a valence bond. Where $K^2$ is a group then preferably q is from 1 to 6, more preferably 1,2 or 3 and most preferably q is 1. When K is a group —(CH$_2$)$_q$NR$^{20}$—, —(CH$_2$)$_q$OC(O)NR$^{20}$, —(CH$_2$)$_q$NR$^{20}$C(O)O—, —(CH$_2$)$_q$NR$^{20}$C(O)—, —(CH$_2$)$_q$C(O)NR$^{20}$— or —(CH$_2$)$_q$NR$^{20}$C(O)NR$^{20}$— then R$^{20}$ is preferably hydrogen, methyl or ethyl, more preferably hydrogen.

Preferably $B^8$ is:

an alkylene group of formula —(CR$^{24}_2$)$_u$—, wherein the groups —(CR$^{24}_2$)— are the same or different, and in each group —(CR$^{24}_2$)— the groups R$^{24}$ are the same of different and each group R$^{24}$ is hydrogen or C$_{1-4}$ alkyl, preferably hydrogen, and u is from 1 to 12, preferably 1 to 6;

an oxaalkylene group such as alkoxyalkyl having 1 to 6 carbon atoms in each alkyl moiety; or an oligo-oxaalkylene group of formula —[(CR 25$_2$)$_v$O]$_w$(CR$^{25}_2$)$_v$— where the groups —(CR$^{25}_2$)— are the same or different and in each group —(CR$^{25}_2$)— the groups R$^{25}$ are the same or different and each group R$^{25}$ is hydrogen or C$_{1-4}$ alkyl, preferably hydrogen, and v is from 1 to 6, preferably 2 or 3, and w is from 1 to 12, preferably 1 to 6.

Preferred groups $B^8$ include alkylene, oxaalkylene and oligo-oxaalkylene groups of up to 12 carbon atoms. In one embodiment BB and $K^2$ contain together up to 12 carbon atoms.

Particular examples of comonomers bearing a reactive group include chloromethylstyrene, methacrylic acid, 2-aminoethylmethacrylate, 2,3-epoxypropyl methacrylate, 3-chloro-2-hydroxypropylmethacrylate, 2-methacryloyloxy-ethyldichlorotriazine, 3-chloro-2-hydroxypropylmethacryl-amide and glycidyl methacrylate and reactive methacrylate esters containing the group HetC(O)O— in which (Het) is a heterocyclic ring, for example benzotriazole or imidazole and reactive methacrylate esters containing a group R$^{16}$OC(O)— in which R$^{16}$ is a succinimido or pentafluorophenyl group.

Particularly preferred comonomers bearing reactive groups are 2-aminoethyl-methacrylate and 3-chloro-2-hydroxypropylmethacrylate.

Comonomers bearing a reactive group capable of binding covalently to a surface, such as those of formula (X) or (XI), are commercially available or may be prepared by conventional techniques using known reactions.

Comonomers of formula (X), which are dichlorotriazine monomers may be prepared in known manner for example by reacting a substituted hydroxy-alkyl(alk)acrylate or aminoalkyl(alk)acrylate with trichlorotriazine in a suitable solvent and in the presence of a base.

Comonomers of formula (XI) which are reactive methacrylate esters in which the ester groups contains an imidazole group may be prepared in known manner by reacting a substituted hydroxyalkyl(alk)acrylate (e.g.2hydroxyethyl-(meth)acrylate), polyethylene-oxide(meth)acrylate or polypropyleneoxide(meth)acrylate with 1,1-carbonyl-diimidazole in a dry solvent. Analogous known methods may be used to prepare succinimido and pentafluorophenyl methacrylate-esters of formula (X), by reaction with a reactive ester, acid halide or acid anhydride.

Where comonomers containing a reactive group are used to crosslink a copolymer, it will be appreciated that not all of the reactive groups need necessarily crosslink and that groups not so bound may participate in other chemistry. Such groups may in particular provide points for the attachment of moieties such as ligands to the polymer, when coated onto a substrate.

Comonomers containing a reactive group, such as compounds of formula (X) and (XI) are particularly useful as comonomers containing crosslinkable groups, which react with other crosslinkable groups, rather than a monomer which bind covalently to a surface.

The crosslinkable groups and/or the copolymerisation conditions will be chosen so that they will not crosslink when the comonomers are copolymerised; thus the polymerisation product will be an uncrosslinked linear copolymer which may be subsequently crosslinked after coating the copolymer onto a surface so as to improve the stability of the coating. When such crosslinking between linear polymer chains is employed the crosslinkage may be formed either between two such crosslinkable groups or between a crosslinkable group and a non-inert group in a diluent comonomer residue (defined later). Such a crosslinkage may be formed either by direct reaction of the groups forming the crosslinkage or by reaction of these groups with a reactive bridging molecule for example a reactive gas, such as ammonia.

Residues of such comonomers may therefore be present in polymers which are designed to coat hydrophobic surfaces and containing residues of a comonomer containing an alkyl, fluoroalkyl or siloxane group, which is of formula (VII) or (VIII).

Preferred reactive comonomers which are used to crosslink the comonomer, are those of formula (X) or (XI) in which $Q^2$, or $Q^4$ contains a crosslinkable cinnamyl, epoxy, —CHOHCH$_2$Hal (in which Hal is a halogen atom), methylol, silyl, an ethylenically unsaturated crosslinkable group, such as an acetylenic, diacetylenic, vinylic or divinylic group, or an acetoacetoxy or chloroalkyl sulfone, preferably chloroethyl sulphone, group.

Particular examples of comonomers bearing a group capable of crosslinking include methacrolein, cinnamyl methacrylate, 2,3-epoxypropyl methacrylate, 3-chloro-2-hydroxypropyl methacrylate, hydroxymethyl methacrylamide, 3-(trimethoxysilyl)propyl methacrylate, 2-acetoacetoxyethyl methacrylate 3-(vinylbenzyl)-2-chloroethyl sulfone.

When a polymer of the invention, containing crosslinkable groups, is coated on a substrate the polymer is in substantially uncrosslinked form. After coating, crosslinking of crosslinkable groups may be performed to increase the strength and stability of the polymer coating.

Diluent Comonomers

In addition to a) the residues of zwitterionic monomer containing a group bearing a centre of permanent positive charge and b) the residues of hydrophobic comonomer, the polymers of the present invention may comprise residues of a diluent comonomer.

Such diluent comonomers may be used to give the polymer the desired physical and mechanical properties. They may be of any known conventional radical polymerisable, preferably ethylenically unsaturated, type compatible with other comonomer(s).

Particular examples of diluent comonomers include alkyl (alk)acrylate preferably containing 1 to 4 carbon atoms in the alkyl group of the ester moiety, such as methyl (alk) acrylate; a dialkylamino alkyl(alk)acrylate, preferably containing 1 to 4 carbon atoms in each alkyl moiety of the amine and 1 to 4 carbon atoms in the alkylene chain, e.g. 2-(dimethylamino)ethyl (alk)acrylate; an alkyl (alk) acrylamide preferably containing 1 to 4 carbon atoms in the alkyl group of the amide moiety; a hydroxyalkyl (alk) acrylate preferably containing from 1 to 4 carbon atoms in the hydroxyalkyl moiety, e.g. a 2-hydroxyethyl (alk) acrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

Other suitable diluent comonomers include polyhydroxyl, for example sugar, (alk)acrylates and (alk)acrylamides in which the alkyl group contains from 1 to 4 carbon atoms, e.g. sugar acrylates, methacrylates, ethacrylates, acrylamides, methacrylamides and ethacrylamides. Suitable sugars include glucose and sorbitol. Particularly suitable diluent comonomers include methacryloyl glucose or sorbitol methacrylate.

Further diluents which may be mentioned specifically include polymerisable alkenes, preferably of 2–4 carbon atoms, eg. ethylene, dienes such as butadiene, alkylene anhydrides such as maleic anhydride and cyano-substituted alkylenes, such as acrylonitrile.

Diluent comonomers may be obtained by conventional known methods.

Of the above diluent comonomers some are inert and act simply to modify the physical and mechanical properties of copolymers containing them. Others, and in particular the hydroxyalkyl(alk)acrylates and polyhydroxyl (alk)acrylates have a reactive role in addition to simply modifying physical and mechanical properties. Such comonomers contain functional groups, such as hydroxyl groups, which may react with a crosslinking group or may react with reactive groups in other molecules to attach them to the copolymer.

It will also be appreciated that alkyl(alk)acrylates containing 6 or more carbon atoms in the alkyl group may be regarded as either diluent comonomers or comonomers capable of binding a polymer to a surface by physisorption. In particular it should be noted that a copolymer which contains such a diluent comonomer and a reactive comonomer capable of reacting at a surface to provide covalent binding to a surface may be used to coat a hydrophillic surface, the reactive comonomer providing binding to the surface and the diluent modifying physical and mechanical properties. However, such a copolymer may also be to coat hydrophobic surfaces, in which the "diluent" monomer will act as a comonomer capable of binding to the surface by physisorption and the comonomer capable of covalent binding will act as a crosslinkable comonomer.

According to a feature of the present invention polymers of the invention may be prepared by copolymerising a monomer containing a zwitterionic group, a comonomer containing a hydrophobic group capable of stably binding the polymer to a surface and optionally a diluent and/or crosslinkable comonomer.

Any conventional technique may be used for polymerisation, typically thermal or photochemical polymerisation. Where comonomers capable of producing crosslinking in the coated polymer film are present, the polymerisation condition are set such that crosslinking does not occur during polymerisation. Thus, for example, actinic radiation would not be used to prepare a polymer containing a comonomer which can form crosslinks by exposure to actinic radiation.

For thermal polymerisation a temperature from 40 to 100° C., typically 50 to 80° C. is used. For photochemical polymerisation actinic radiation such as gamma, U.V., Visible or microwave radiation may be used. Typically U.V. radiation of wavelength 200 to 400 nm is used.

The polymerisation is generally performed in a reaction medium, which is for instance a solution or dispersion using as a solvent for example acetonitrile, dimethyl formamide, chloroform, dichloromethane, ethyl acetate, dimethyl sulphoxide, dioxan, benzene, toluene, tetrahydrofuran, or where the polymer does not contain groups which react with protic solvents, water or an alkanol containing from 1 to 4 carbon atoms, e.g. methanol, ethanol or propan-2-ol. Alternatively, a mixture of any of the above solvents may be used.

The polymerisation may be carried out in the presence of one or more polymerisation initiators, such as benzoyl peroxide, 2,2'-azo-bis(2-methylpropionitrile) or benzoin methyl ether. Other polymerisation initiators which may be used are disclosed in "Polymer Handbook", 3rd edition, Ed. J. Brandrup and E. H. Immergut, Pub. Wiley-Interscience, New York, 1989.

Generally the copolymerisation is performed for 1 to 72 hours, preferably 8 to 48, for instance 16 to 24 hours, and under an inert atmosphere of for example nitrogen or argon. The polymer is generally purified by dialysis, precipitation in a non-solvent (e.g. diethyl ether or acetone) or ultrafiltration. The resulting polymer is generally dried under vacuum, eg. for 5 to 72 hours and has a molecular weight from 10,000 to 10 million, preferably from 20,000 to 1 million.

The precise proportion and nature of the various monomers used to prepare a copolymer according to the present invention comprising residues of a zwitterionic monomer and a comonomer containing a hydrophobic group may be adjusted to provide a copolymer which is particularly suitable for coating a particular surface. Thus the proportion of comonomer containing a hydrophobic group may be adapted to provide efficient physisorption at a particular hydrophobic surface. Similarly the proportion of the zwitterionic monomer and of diluent and/or crosslinkable comonomer may be adapted to provide the desired biocompatibility and physical and mechanical properties. It will be appreciated that to obtain the desired combination of properties more than one type of zwitterionic monomer, comonomer containing a hydrophobic group or crosslinkable and/or diluent comonomer may be used.

Similarly, the nature of the zwitterionic and hydrophobic groups may be adjusted to provide the desired biocompatibility and efficient binding at a particular surface, as well as desired physical and mechanical properties. Where, in addition, a diluent and/or crosslinkable comonomer is used the nature of the diluent and/or crosslinkable comonomer and the proportions of the comonomers may be likewise adjusted. It will again be appreciated that to obtain the desired combination of properties more than one type of zwitterionic monomer and comonomer containing a hydrophobic group and/or more than one type of crosslinkable and/or diluent comonomer may be used.

The monomer composition which is subjected to polymerisation to provide a polymer according to the invention comprises a minimum of 0.01%, preferably 1%, more preferably 5% by weight of zwitterionic monomer and a maximum of 99.9%, preferably 99%, more preferably 95% by weight of other monomer. Such other monomer includes the comonomer containing a hydrophobic group, a diluent monomer or monomers and/or a crosslinkable monomer or monomers.

The monomer composition further comprises a minimum of 0.01%, preferably 1%, more preferably 5% by weight of comonomer containing a hydrophobic group and a maximum of 99.9%, preferably 99%, more preferably 95% by weight of other monomer or monomers. Such other monomer may be a diluent monomer or monomers and/or a crosslinkable monomer or monomers.

Preferably the monomer composition comprises no more than 95%, more preferably no more than 90% and even more preferably no more than 80% by weight of comonomer containing an alkyl, fluoroalkyl or siloxane group which is capable of binding the polymer to a surface by physisorption the balance of the composition being zwitterionic monomer, diluent monomer or monomers and/or crosslinkable monomer or monomers. Such a composition typically comprises up to 50% by weight of diluent comonomer. Where diluent comonomer is present, it preferably comprises at least 1%, more preferably 5%, by weight of the total comonomer composition. Where present, crosslinkable comonomer or comonomers generally comprise from 0.1% to 20% by weight of the total comonomer composition.

Preferably the molar ratio in the copolymer of zwitterionic monomer residues to comonomer residues is from 5:95 to 80:20, more preferably 10:90 to 50:50. In addition the copolymer preferably comprises from 5% to 50%, more preferably 10% to 25%, by mole residues of diluent monomer and/or from 0.1 to 20%, more preferably 1% to 10%, by mole residues of crosslinkable comonomer, provided that where residues of both diluent and crosslinkable comonomer are present, they do not exceed in combination 50%, preferably 35% by mole.

In addition the monomer or comonomer composition may comprise further components such as a polymerisation initiator, chain transfer agent, acid, base, surfactant, emulsifier or catalyst of conventional type each in an amount from 0.1% to 5%, typically from 0.2% to 3% and preferably about 0.5%, by weight each relative to the total weight of the monomers.

As a further feature the present invention provides a process for biocompatibilising a surface which comprises coating the surface with a polymer according to the present invention. Various types of surfaces may be coated depending upon the nature of the groups in the polymer capable of binding it to the surface.

Polymers containing residues of monomers containing alkyl, fluoroalkyl or siloxane groups capable of binding the polymer to a surface by physisorption are particularly suitable for coating hydrophobic surfaces, e.g. polyethylene, polypropylene and polytetrafluoroethylene (PTFE) surfaces; fluorine containing polymers of the invention being particularly suited to coating PTFE surfaces.

Hydrophillic surfaces may be rendered hydrophobic and suitable for coating with such polymers by known methods (see for example "Chemical Reactions of Polymers" Ed. E.M. Fettes, 1964, Interscience, London).

Treatment with such a polymer is generally carried out by coating the surface with a solution, dispersion (including a microdispersion) of the polymer, generally in an alcoholic, aqueous, organic or halogenated solvent or a mixture thereof, e.g. methanol, ethanol, dichloromethane, trifluoromethanol or freon. The treatment is generally carried out at ambient or elevated temperature, such as from 5 to 60° C.

In one specific embodiment of the invention, the copolymer is coated onto the substrate in the form of a microdispersion for example a microemulsion.

After coating the polymer may be crosslinked if it contains the residues of crosslinkable comonomer by known method for crosslinking the specific crosslinkable groups which are present. Crosslinking may, for instance, be introduced thermally, using actinic radiation, using reactive gases for example ammonia by changing the pH, using difunctional additives or by using activation chemistries for example by known methods as described in "Methods in Enzymology, volume 135, Immobilised Enzymes and Cells, part B", Ed. K. Mosbach, Academic Press Inc, New York, 1987. This activation may be performed on the dry coating, in the cases of thermal radiation or gas treatment. Alternatively for cases where the pH needs to be changed or additives need to be included, activation may be performed on the coated material in a solution which does not remove the coating.

Materials may be coated with polymers of the invention by known techniques, such as dip-coating, spray-coating, web-coating or spin coating.

Materials having surfaces coated according to the present invention can be used as a construction material for implants or prostheses for the human or animal body, particularly where these implants or prostheses are to come into direct physical contact with blood and where biocompatibility and particularly haemocompatibility are required e.g. in heart valves. They can also be used in the construction of membranes and other devices that are to be brought into contact with blood or other body fluids on an extra-corporeal basis, for example in heart-lung machines or artificial kidneys.

Additionally the polymers of the invention can be used to coat materials employed in down stream processing applications e.g. separation membranes and process equipment and tubing. In particular the materials of the invention can be used to modify the surface properties of biofiltration membranes in bioreactors and fermentation systems, where the membranes come into direct contact with complex biological solutions containing e.g. proteins, polysaccharides, fats and even whole cells. The polymers of the invention are particularly useful in reducing membrane fouling by the components of a process solution.

When the polymers of the present invention are used to coat the surface of a material which is then used in the construction coat of finished devices, it may be necessary to take precautionary steps to ensure that the coated surface is not damaged and the effectiveness of the treatment reduced before the finished device is produced.

In addition, the polymers of the present invention can be used to coat finished implants, prostheses, membranes, catheters, contact lenses, intraocular lenses, and other devices which are coated with a polymer according to the present invention to impart biocompatibility to the article.

The invention thus also provides a finished device comprising a surface having a coating thereon of a polymer of the present invention.

The present invention will now be further illustrated by the following Examples:

EXAMPLES

The following assays have been used to evaluate coatings of polymers according to the present invention.

Protein Adsorption using an Enzyme Immunoassay

The assay determines adsorption of human fibrinogen at a surface. This protein is representative of protein which is typically adsorbed at a surface. The assay can be readily modified to determine the adsorption of other proteins.

Discs (7 mm in diameter) of untreated material (as controls) and material treated with polymer as described below, were prepared and washed with phosphate buffered saline (PBS) for at least 10 minutes in the wells of microplates. The samples were incubated with human plasma (300 µl) for 10 minutes and then washed with PBS three times. Each of the test samples and each of the control samples were treated with human fibrinogen-specific antibody (300 µl) for 30 minutes and again washed with PBS three times. As a control for non-specific binding of antibody to the samples, each sample was also incubated with non-specific antibody (300 µl) for 30 minutes. A conjugate of horseradish peroxidase and a second antibody specific to the first antibody (300 µl) was added to both the test samples and the controls and incubated for 30 minutes before washing. Each of the test samples and the controls were transferred to new microplates and a solution of 2,2'-azino-bis(3-ethyl benzthiazoline-6-sulphonic acid) (ABTS) in phosphate-citrate buffer (300 µl, 0.6 mg/ml) added, the reaction was allowed to proceed for 10 minutes. At this time an aliquot of the mixture (200 µl) was removed and added to a solution of citric acid and sodium azide in distilled water (20 µl, 0.21 g/ml and 2mg/ml respectively). The optical density of the solutions was measured using a Techgen automated plate reader at 650 nm using the ABTS solution as blank.

In an alternative procedure, rather than using ABTS, each of the samples was transferred to wells of new microplates and a solution of o-phenylene diamine (OPD) in phosphate-citrate buffer (300 µl, 0.4 mg/ml) added, and the reaction was allowed to proceed for 10 minutes. At this time an aliquot of the mixture (200 µl) was removed from each well and the optical density of the solutions was measured using a Techgen automated plate reader at 450 nm using the OPD solution as blank.

Activated Platelet Study

Blood was collected from a healthy adult volunteer using the double syringe method where the first 5 ml of blood is discarded. The blood was collected into tri-sodium citrate (32 g/l) in the proportion of 9 volumes to 1 volume citrate in plastic tubes. The samples were kept at room temperature on a spiral mixer until used.

Discs (7 mm in diameter) of untreated material as controls and material treated with polymers as described below were prepared and placed into the wells of a microplate. The samples were incubated with whole fresh citrated blood (200 µl) on a rotary mixer for 30 minutes before washing in PBS four times. Platelet activation was measured by a proprietary assay [Lindon, J. N. et al., *Blood*, 68, 355 (1986)] and British Patent Application No. 91-25721.2].

In an alternative procedure half of the test replicates were incubated with citrated blood (200 µl) and the remainder were incubated with EDTA-treated blood on a phase shaker for 30 minutes before washing in PBS four times. Platelet activation was measured in a manner similar to that described above for detection of proteins by enzyme immunoassay using antibodies against GMP140 to detect the presence of this platelet activation marker on the surface of biomaterials. In the presence of EDTA, which extracts calcium from inside platelets, activation is inhibited, so that incubation with EDTA-treated blood acts as a non-specific control for activation, obviating the need for incubation in non-specific antibody.

C-Reactive Protein (CRP) Binding Assay

C-reactive protein is a protein which binds specifically to isolated ammonium phosphate esters groups e.g. phosphoryl choline groups which are attached to a surface.

Discs (7 mm in diameter) of untreated material and material treated with polymer as described below, were prepared and washed with HEPES-buffered saline (HBS) for a least 10 minutes in the wells of microplates. The samples were incubated in quadruplet for 45 minutes in a protein solution consisting of bovine serum albumin (BSA) (40 mg/ml) and CRP (0.012 mg/ml) in HBS and containing calcium chloride (1 mM). In parallel, identical samples (both coated and uncoated) were incubated either in BSA/Ca$^{2+}$ solution in the absence of CRP, in BSA/CRP/Ca$^{2+}$solution in the presence of soluble phosphoryl choline (1.5 mg/ml) or in BSA/CRP solution containing EDTA (20 mM) rather than calcium chloride.

After incubation, all the samples were washed in phosphate buffered saline (PBS) three times and then incubated for 1 hour in 300 µl of a 1:100 dilution of commercially available anti-CRP antibody conjugated with horseradish peroxidase. The samples were washed three times in PBS as before and transferred to new microplates. A solution of o-phenylene diamine (OPD, 0.4 mg/ml) in phosphate-citrate buffer was added and the reaction allowed to proceed for ten minutes. At this time an aliquot of the mixture (200 µl) in each of the wells was transferred to a new well, and the optical density of the solutions measured using a Techgen automated plate-reader at 450 nm using the OPD solution as a blank.

A positive control containing isolated phosphoryl choline groups may be provided using beaded agarose immobilised with p-aminophenylphosphoryl choline. The specificity of CRP binding may be demonstrated by inhibition by phosphoryl choline and dependance upon the presence of calcium.

Example 1
Preparation of Poly N,N-dimethyl-N-(2-methacrovloxyethyl)-N-3-sulphopropyl) ammonium betaine inner salt-co-n-dodecylmethacrylate) 1:2

The copolymer mentioned in the heading was synthesized using a method similar to that used on comparative example 1 (see below), but using the sulphobetaine synthesized in reference example 1 in stoichometrically equivalent quantity in place of the ammonium phosphate inner salt.

Example 2
Preparation Method for poly (N,N-Dimethylammonium-N-Propylsulphonate-N-Ethylmethacrylate)-co-(1H,1H,2H,2H,-Heptadecafluorodecyl Methacrylate) 1:2

N-N-dimethylammonium-N-propylsulphonate-N-ethylmethacrylate (4.565 g), 1H,1H,2H,2H,-heptadecafluorodecyl methacrylate (17.413 g), AIBN (0.1316 g), ethyl acetate (34 ml) and 2,2,2-trifluoroethanol (86 ml) was transferred to a three port reaction flask. The solution mix was heated to 65 C for 48 hours using a nitrogen blanket and water condenser. Once the reaction has completed the solvent was extracted on the rotary evaporator. The crystalline polymer was then recrystallised twice using a 2,2,2-trifluoroethanol/trifluoroacetic acid mix (ratio 4:1), into acetone (350 ml). The resulting polymer (80% yield), was dried under vacuum.

Example 3
Preparation Method for Poly (Dimethylammonium-N,N-Propylsulphonate-N-Ethylmethacrylate)-co-(1H,1H,2H,2H,-Heptadecafluorodecyl Methacrylate) 1:1

N,N-Dimethylammonium-N-propylsulphonate-N-ethylmethacrylate (4.565 g), 1H,1H,2H,2H,-hepadecafluorodecyl methacrylate (8.696 g), AIBN (0.1318 g), ethyl acetate (34 ml) and 2,2,2-trifluoroethanol (86 ml) was transferred to a three port reaction flask. The solution mix was heated to 65 C for 48 hours using a nitrogen blanket and water condenser. Once the reaction has completed the solvent was extracted on the rotary evaporator. The crystalline polymer was then recrystallised twice using a ,2,2-trifluoroethanol/trifluoroacetic acid mix (ratio 4:1), into acetone (350 ml). The resulting polymer (80% yield), was dried under vacuum.

Comparative Example 1
Preparation of Poly(2-(methacryloyloxyethyl)-2'-(trimethylammonium)ethyl Phosphate inner salt -co-n-dodecyl methacrylate) (1:2)

2-(Methacryloyloxyethyl)-2'-(trimethylammonium)ethyl phosphate inner salt (5.0 g, 0.0170 mole) and n-dodecylmethacrylate (8.55 g, 0.0340 mole) were dissolved in methanol/THF (140 ml; 5:9). The solution was stirred (250rpm) at 23° C. under a stream of nitrogen (50 ml/min) for 30 minutes. 2,2'-Azo-bis(2methylpropionitrile)(0.17 g, 1.02 mmole) was added and the flow of nitrogen was reduced to 10 ml/min, the temperature was raised to 60° C. This temperature and nitrogen flow rate were maintained for 16 hours.

The mixture was allowed to cool and vacuum filtered. The filtrate was collected and the polymer precipitated by dropwise addition to acetone (1.21).

The polymer was isolated by filtration under vacuum under a nitrogen atmosphere and finally dried under reduced pressure overnight at room temperature. The resulting polymer (9.5 g, 70%) was a fine white powder.

In an alternative procedure, 2-(methacryloyloxyethyl)-2' (trimethylammonium)ethyl phosphate inner salt (12.06 g, 0.0409 mole) and n-dodecyl methacrylate (20.52 g, 0.0808 mole) were dissolved in propan-2-ol (215 ml) and ethyl acetate (85 ml). The solution was stirred (250rpm) at 23° C. under a stream of nitrogen (50 ml/min) for 30 minutes, 2,2'-azo-bis(2-methylpropionitrile) (0.0645 g, 0.39 mmole) was added and the flow of nitrogen was reduced to 10 ml/min, the reaction temperature was raised to 60° C. This temperature and nitrogen flow rate were maintained for 40 hours.

The mixture was allowed to cool and vacuum filtered. The filtrate was evaporated to dryness using a rotary evaporator and dissolved in dichloromethane (120 ml) and methanol (10 ml). The polymer was isolated from this mixture by precipitation in acetone (2500 ml), vacuum filtration and drying. The polymer was redissolved in dichloromethane (100 ml) and methanol (30 ml) and isolated as described above.

The resulting polymer, obtained in 70–80% yield was a white powder.

NMR(20OMHZ, d, ppm, $CD_3OD/CDCl_3$) 4.2–4.4 (b), 3.8–4.2 (b), 3.6–3.8 (b), 3.3 (s), 1.8–2.2 (b), 1.5–1.8 (b), 1.2–1.5 (s), 0.8–1.0 (s)

IR($cm^{-1}$, KBr disc) 3430, 2929, 2854, 1732, 1469, 1246, 1156, 1089, 968, 788.

Elemental Analysis theory $C_{64.5,}$ H 9.9, N 1.8, P 3.9 actual $C_{59.0,}$ H 10.0, N 1.8, P 3.9

The polymer had a relative viscosity in ethanol: chloroform (50:50) at 25° C. of 1.13±0.02 (when prepared using methanol: THF as solvent) and 1.26±0.02 (when prepared using propan-2-ol: ethylacetate as solvent).

Comparative Example 2
The coating of poly(ethylene) ribbon with Poly(2-(methacryloyloxyethyl)-2'-(trimethylammonium)ethyl phosphate inner salt -co- n-dodecyl methacrylate (1:2)

Poly(ethylene) ribbon was washed with ethanol and allowed to dry in the air. The poly(2(methacryloyloxyethyl) 2'(trimethylammonium)ethyl phosphate inner salt -co-n-dodecyl methacrylate) (1:2) (50 mg) was dissolved in ethanol/chloroform (5 ml, 40:1) and the poly(ethylene) coated by a one stage mechanical dip-coating procedure drawing the ribbon through the solution slowly. The coated ribbon was allowed to dry in a dust free atmosphere at room temperature.

The treated poly(ethylene) showed a 65% reduction in protein adsorption as compared to the untreated material and a 83% reduction in platelet activation (determined using the assay of Lindon et al) as compared to the untreated material.

In the C-reactive protein binding assay, no binding of CRP was observed to the treated poly(ethylene). In contrast, CRP binding was observed for a positive control. The specificity of this CRP binding was demonstrated by the fact that it was inhibited by phosphoryl choline and dependence upon the presence of calcium.

According to an alternative procedure, polyethylene ribbon was washed in propan-2-ol and coated with the copolymer dissolved in propan-2-ol (1 g in 100 ml) at 40° C. using an otherwise analogous manner.

Comparative Example 3
Preparation of Poly(2-(methacryloyloxyethyl)-2'-(trimethylammonium)ethyl phosphate inner salt-co-n-dodecyl methacrylate-co-1H,1H,2H,2H-heptadecafluorodecyl methacrylate This example describes the preparation of a terpolymer containing a fluorinated monomer in addition to the phosphorylcholine group, for physisorption onto a surface. 2.7 g 2-(methacryloyloxyethyl)-2'-(trimethyl-ammonium) ethyl phosphate inner salt, 2.35 g n-dodecyl-methacrylate, 4.92 g 1H,1H,2H,2H-heptadecafluorodecyl methacrylate and 0.0162 g AIBN were stirred at 60° C. in isopropanol (50 ml)/ethyl acetate (50 ml) under a nitrogen atmosphere for 40 hours. After removal of the solvent the polymer was recovered by precipitation from dichloromethane into acetone. Yield 8.34 g.

Example 4
Coating onto polyethyleneterephthalate

The copolymers of comparative examples 1 and 3 and examples 1 to 3 were coated from solutions in ethanol (in the case of comparative examples) or 2,2,2-trifluoroethanol (in the case of examples 1 and 3) of concentration 10 mg/ml by dip coating onto strips of polyethylene terephthalate and dried. The dried coated substrates were subjected to the fibrinogen adsorption assay.

The results show that comparative examples 1 and 3, which are known by the assignee to be useful as biocompatibilising polymers, give fibrinogen adsorption values reduced by amounts of more than 75 or 80% for comparative example 1 and for comparative example 3. The reductions shown by the polymers of the invention are 35% for example 3 and 20% for example 2 and 75 or 85% for example 1.

Reference Example 1
Synthesis of N,N-dimethyl-N-(2-methacroyloxyethyl)-N-(3-sulphopropyl) ammonium betaine inner salt 2 (Dimethylamino)ethylmethacrylate was vacuum distilled and then dissolved in 0.1M dichloromethane. To this solution was added an equimolar amount of propane sultone. The betaine slowly precipitated out of solution and was recovered by filtration and washed with cold dichloromethane. The reaction is shown in Reaction Scheme B.

Reference Example 2
Preparation of 2 (methacryloyloxyethyl)-2 (trimethylammonium ethyl phosphate inner salt The preparation is illustrated by the reaction scheme A which follows.
a) 2-Chloro-1,3-dioxapholane (1)
In a flask fitted with a pressure equalising dropping funnel, reflux condenser (fitted with a CaCl$_2$ guard tube) and magnetic stirrer, was placed a solution of phosphorus trichloride (220 ml; 346.3 g; 2.52 mol) in dichloromethane (500 ml). Ethylene glycol (139 ml; 154.7 g, 2.49 mol) was then added dropwise via the dropping funnel at such a rate that the evolution of HCl did not become too excessive. On the addition of the ethylene glycol, the condenser was arranged for distillation, and the dichloromethane removed at atmospheric pressure. When the distillate temperature reached 60° C. the flask was arranged for 5 vacuum distillation using a water pump, Distillation then gave 2-chloro-1,3-dioxapholane (158 ml; 224.5 g; 71.3) as a colourless mobile liquid (which fumes in moist air) b.pt. 36–40° C./21 mm Hg. [cf 45.5–47° C./20 mm Hg, Lucas et al, J. Am. Chem. Soc., 72, 5491, (1950)]. IR (cm$^{-1}$, thin film) 2980, 2905, 1470, 1210, 1005, 930, 813, 770.
b) 2-Chloro-2-oxo-1,3,2-dioxaphospholane (2)

In a flask fitted with a magnetic stirrer, reflux condenser (fitted with a CaCl$_2$ guard tube) and sintered glass gas inlet tube, was placed a solution of 2-chloro-1,3,2-dioxaphospholane (100.8 g; 0.797 mol) in dry benzene (200 ml). The solution was stirred and a steady stream of oxygen was bubbled through the solution. The reaction was mildly exothermic, and temperature control was achieved by allowing the solvent to reflux. The oxygen was passed through the reaction mixture for 6 hours. The solvent was removed by rotary evaporation, and the colourless mobile residue distilled to give 2-chloro-2-oxo-1,3,2-dioxaphospholane (2) (87.41 g; 77%) as a colourless mobile liquid -b.pt 95–97° C./0.2mbar [c.f. 102.5–105° C./1 mbar (Edmundson, Chem. Ind. (London)), 1828 (1962); 79° C./0.4mbar (Umeda et al., Makromol. Chem. Rapid Commun., 3, 457, (1982)].

IR(cm$^{-1}$, thin film) 2990, 2910, 1475, 1370, 1310, 1220, 1030, 930, 865, 830.

c) 2(2-Oxo-1,3,2-dioxaphospholan-2-yloxy)ethyl methacrylate (3)

In a flask fitted with a magnetic stirrer, low temperature thermometer, and a pressure equalising funnel fitted with a silica gel guard tube; was placed a solution of 2-hydroxyethylmethacrylate (20.00 g, 0.154mol) and triethylamine (15.60 g; 0.154mol) in dry diethyl ether (300 ml). The solution was stirred and cooled to between –20° C. and –30° C. A solution of freshly distilled 2-chloro-2-oxo-1,3,2-dioxaphospholane(2) (21.9 g; 0.154 mol) in dry diethyl ether (20 ml) was then added dropwise over 30 minutes, the temperature being held at –20° C. during the addition. Stirring was continued at this temperature for a further 1 hour and then for a further hour as the reaction mixture was allowed to warm to room temperature. The precipitated triethylamine hydrochloride was removed by filtration, and was washed well with dry ether. The ether was removed from the combined filtrate and washings by rotary evaporation. The cloudy oil residue was then shaken for 5 minutes with dry diethyl ether (50 ml) to precipitate a further crop of triethylamine hydrochloride, which was again removed by filtration. Removal of the ether on the rotary evaporator gave (3) (34.18 g; 94.3%) as a colourless viscous oil. IR (cm$^{-1}$, thin film) 1720, 1640, 1450, 1360, 1310, 1290, 1170, 1030, 930, 850.

NMR (CDCl$_3$; 60 MHz, δ ppm) 1.95 (s,3H), 4.25–4.70 (m,8H), 5.70 (m,1H), 6.25 (m,1H). Rf 0.9 (SiO$_2$, eluting with 10% methanol: 90% dichloromethane; spot visualised with molybdenum blue spray reagent and with iodine vapour).

d) 2(Methacryloyloxyethyl)-2'(trimethylammonium)ethyl phosphate inner salt (4).

The pholane (3) (67.20 g; 0.285 mol) was dissolved in 100 ml of dry acetonitrile, and placed in a heavy walled tissue culture bottle. The pholane solution was then treated with a solution of anhydrous trimethylamine (25.74 g; 0.436 mol) in dry acetonitrile (100 ml). The vessel was then sealed, and placed in a water bath held at 50° C. for 30 hours. The vessel was opened, and the solution brought to the boil. The solution was filtered whilst hot, and then set aside for crystallisation.

The product was collected by filtration, and most of the solvent removed by suction. The wet product was then washed thoroughly with anhydrous ether, then dried under reduced pressure, to give (4) as a white amorphous, hygroscopic solid (51.16 g; 61%). Evaporation of the mother liquor gave a very viscous oil (20.00 g; 23%), from which further product (4) crystallised on standing at –200 C. TLC (silica gel plates, eluting with methanol/dichloromethane (1:1 v/v)) showed one spot Rf 0.1, which was revealed with Dragendorff's reagent, Molybdenum blue spray reagent, and iodine vapour. IR(cm$^{-1}$ 1720, 1640, 1320, 1300, 1230, 1170, 970, 750.

NMR (D$_2$O; 60 MHz; 5 ppm) 2.0 (s,3H), 3.27 (s,9H) 3.60–4.50 (m, 8H), 5.80, (m,1H) and 6.25 (m,1H).

CHN Found: C$_{42.98}$%, H 7.88%, N 4.42%, P 10.51%.
CHN Theory: C$_{44.75}$%, H 7.46%, N 4.75%, P 10.51%.

Reaction Scheme A

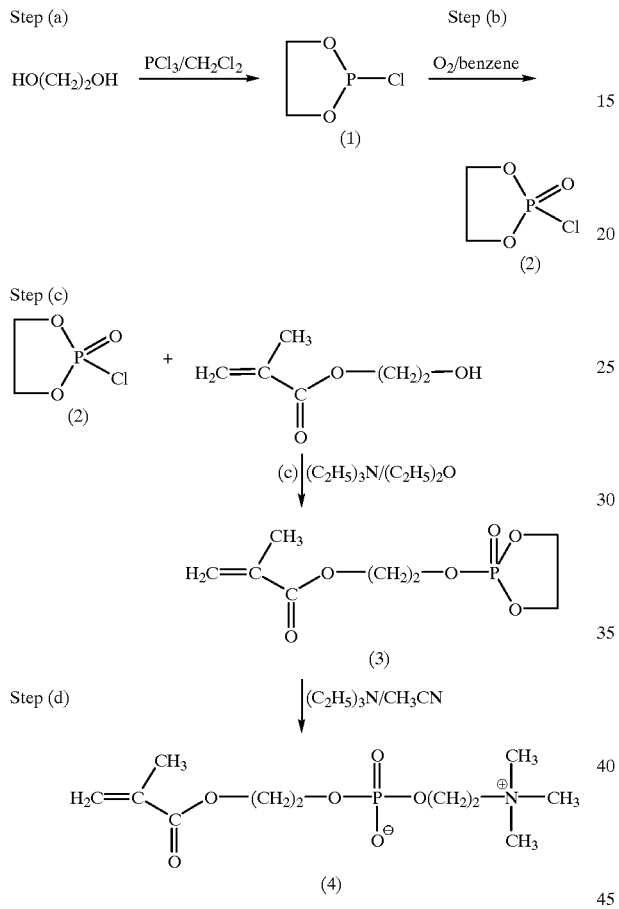

Reaction Scheme B

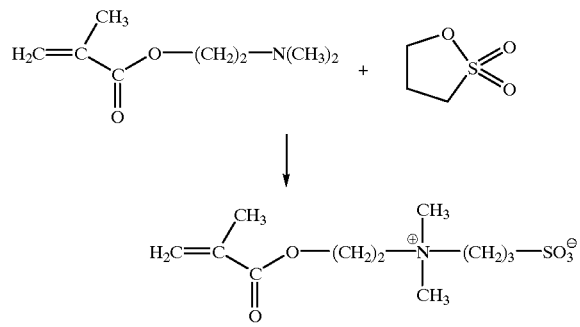

What is claimed is:

1. A non-crosslinked biocompatible polymer formed from an ethylenically unsaturated monomer consisting essentially of (a) a radical polymerisable ethylenically unsaturated zwitterionic monomer containing a zwitterionic group having formula (I):

$$Y-B-X \qquad (I)$$

wherein
B is a straight or branched alkylene;
Y is an ethylenically unsaturated polymerisable group

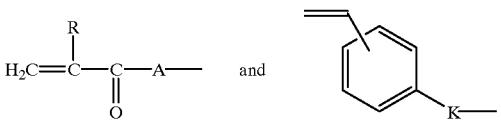

wherein R is hydrogen or a C$_1$–C$_4$ alkyl group;
A is —O— or —NR$^1$— where R$^1$ is hydrogen or a C$_1$–C$_4$ alkyl group; and
X is a zwitterionic group IVB

(IVB)

where the groups R$^6$ are the same or different and each is hydrogen or C$_{1-4}$ alkyl and d is 2 to 4; and (b) a comonomer of formula (VI)

$$Y^1-Q \qquad (VI)$$

where Y$^1$ is an ethylenically unsaturated polymerisable group

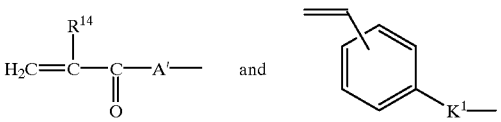

where R$^{14}$ is hydrogen or C$_1$–C$_4$ alkyl,
A' is —O— or NR$^{15}$— where R$^{15}$ is hydrogen or a C$_1$–C$_4$ alkyl group and
Q is the hydrophobic group and is selected from the group consisting of C$_{6-24}$-alkyl groups;
with a molar ratio of zwitterionic monomer to comonomer in a range 10:90 to 50:50.

2. A polymer according to claim 1 in which the group Q is a straight or branched alkyl group containing 8 to 24 carbon atoms.

3. A polymer according to claim 1 in which each R$^{17}$ is hydrogen and m is 7–11.

4. A polymer according to claim 1 in which Q is a fluoroalkyl group of formula (CR$^{17}_2$)$_m$CR$^{17}_3$ wherein the groups (CR$^{17}_2$) are the same or different and in each group (CR$^{17}_2$) the groups R$^{17}$ are the same or different and each group R$^{17}$ is selected from the group consisting of hydrogen or C$_{1-4}$-alkyl C$_{1-4}$-fluoroalkyl and fluorine, provided that at least one of the groups R$^{17}$ is fluorine or fluoroalkyl, and m is 1 to 23.

5. A polymer according to claim 4 in which the comonomer is 1H, 1H, 2H, 2H-heptadecylfluoro-decylmethacrylate.

6. A polymer according to claim 1 in which Q is a siloxane group —$(CR^{16a}{}_2)_{qq}(SiR^{16b}{}_2)(OSiR^{16b})_{pp}R^{16b}$ in which each group $R^{16a}$ is the same or different and is hydrogen or $C_{1-4}$-alkyl, each group $R^{16b}$ is alkyl of 1 to 4 carbon atoms, qq is from 1 to 6 and pp is from 0 to 49.

7. A polymer according to claim 6 in which the comonomer is mono-3-methacryloyloxypropyl-terminated polydimethyl siloxane.

8. A polymer according to claim 1 in which the ratio of zwitterionic monomer to comonomer is in the range 5:95 to 80:20.

9. A polymer according to claim 4 in which the ratio of zwitterionic monomer to comonomer is in the range 5:95 to 80:20.

10. A polymer according to claim 1 formed from monomers including 5 to 50% by mole of diluent monomer which is a radical polymerisable ethlyenically unsaturated compound not having said zwitterionic group or said hydrophobic group.

11. A polymer according to claim 2 formed from monomers including 5 to 50% by mole of diluent monomer not having said zwitterionic group or said hydrophobic group.

12. A polymer according to claim 4 formed from monomers including 5 to 50% by mole of diluent monomer not having said zwitterionic group or said hydrophobic group.

* * * * *